(12) United States Patent
Brown et al.

(10) Patent No.: US 6,348,452 B1
(45) Date of Patent: Feb. 19, 2002

(54) ALTERATION OF MICROBIAL POPULATIONS IN THE GASTROINTESTINAL TRACT

(75) Inventors: Ian L. Brown, Tamworth; Patricia Lynne Conway, La Perouse; Anthony John Evans, Pennant Hills; Karl Anders Olof Henriksson, Bellevue Hill; Kenneth J. McNaught, Cottage Point; Xin Wang, Randwick, all of (AU)

(73) Assignees: The University of New South Wales; Burns Philp & Company; Burns Philp Research & Development PTY LTD, all of New South Wales; Commonwealth Scientific and Industrial Research Organisation, Australian Capital Territory; Arnott's Biscuits Limited, New South Wales; Gist-Brocades Australia PTY Limited, New South Wales; Goodman Fielder Ingredients Limited, New South Wales, all of (AU)

( * ) Notice: Subject to any disclaimer, the term of this patent is extended or adjusted under 35 U.S.C. 154(b) by 0 days.

(21) Appl. No.: 09/155,116

(22) PCT Filed: Mar. 20, 1997

(86) PCT No.: PCT/AU97/00174

§ 371 Date: Jan. 29, 1999

§ 102(e) Date: Jan. 29, 1999

(87) PCT Pub. No.: WO97/34591

PCT Pub. Date: Sep. 25, 1997

(30) Foreign Application Priority Data

Mar. 20, 1996 (AU) .................................................. PN8810
Mar. 20, 1996 (AU) .................................................. PN8811
Mar. 20, 1996 (AU) .................................................. PN8812
Mar. 20, 1996 (AU) .................................................. PN8814

(51) Int. Cl.[7] ............................................. A61K 31/715
(52) U.S. Cl. ........................................ 514/60; 424/93.4
(58) Field of Search .......................... 514/60; 424/93.4

(56) References Cited

U.S. PATENT DOCUMENTS 5,143,845 A * 9/1992 Masuda ................... 435/252.4
5,147,668 A    9/1992 Munk .......................... 426/61

FOREIGN PATENT DOCUMENTS

| AU | 21247/67  | 11/1968 |
| EP | 0659769   | 6/1995  |
| JP | 8-310960  | 11/1996 |
| WO | 96/08261  | 3/1996  |

OTHER PUBLICATIONS

Nutrition Reports International, vol. 15, No. 2, Feb. 1977, Bruns et al, "Effect of Modified Starch on the Microflora of the Small Intestine and Caecum of Rats", pp. 131–138.
Japan Patent 0621773 A. Nov. 1992 (see the enclosed abstract).*

* cited by examiner

*Primary Examiner*—Kevin E. Weddington
(74) *Attorney, Agent, or Firm*—McDermott, Will & Emery

(57) ABSTRACT

Method of enhancing a resident population of microorganism in a selected site of the gastrointestinal tract of an animal, the method comprising providing to the animal a selected modified or unmodified resistant starch or mixtures thereof in combination with one or more probiotic microorganisms such that upon ingestion the starch passes through the gastrointestinal tract substantially unutilized until it reaches the selected site where it is utilized by the resident and/or the probiotic microorganisms thereof causing an increase in number and/or activity of the microorganisms.

17 Claims, 15 Drawing Sheets

Group A: Waxy starch plus S. typhimurium and B. bifidum
Group B: Hi Maize starch starch plus S. typhimurium and B. bifidum
Group C: Modified amylose A 955 D2 plus S. typhimurium and B. bifidum
Group D: Hi Maize starch plus S. typhimurium only
Group E: Normal mice diet plus S. typhimurium only Group 1: Waxy starch plus Bif. X8AT2
Group 2: Hi maize starch plus Bif. X8AT2
Group 3: Carboxymethylated high amylowe starch plus Bif. X8AT2
Group 4: Hi maize starch plus medium
Group 5: Normal mice diet plus Blf. X8AT2

ALTERATION OF MICROBIAL POPULATIONS IN THE GASTROINTESTINAL TRACT

TECHNICAL FIELD

This invention relates to methods of enhancing resident populations of microorganisms or suppressing undesirable populations of microorganisms at selected sites of the gastrointestinal tract of animals including humans. As used in this specification, probiotic or probiotic microorganism is a live microbial feed supplement which beneficially affects the host animal by improving its intestinal microbial balance. This is the definition provided by R. Fuller (AFRC Institute of Food Research, Reading Laboratory, UK) in—Journal of Applied Bacteriology, 1989. 66, pp.365–378. "Probiotics in Man and Animals—A Review", and has subsequently been extended to include supplements and food for humans.

BACKGROUND ART

The gastrointestinal tract microflora of the healthy subject protects the host from pathogen invasion. In the young, the elderly and the compromised patient, however, this protective barrier is less effective. An individual can be compromised to various degrees ranging from minor stress and related events, for example, dietary changes, emotional and nutritional stresses, to extreme cases such as in immunocompromised patients and patients undergoing radio- and chemotherapy.

Probiotic bacteria have been described to exert antimicrobial effects which refers to the actions of the probiotic preparation on another microbe or group of microbes in the gastrointestinal tract. These are directly applicable to the use of probiotics for enhanced resistance against intestinal pathogens, prevention of diarrhoea and constipation. The types of interactions include competitive colonisation as well as adhesion and growth inhibition.

Competitive colonisation refers to the fact that the probiotic strain can successfully out-compete the pathogen for either nutrients or the site of colonisation. Since many gastrointestinal pathogens attach to the intestinal mucosa as the first step in infection, it would be beneficial to the host if this adhesion could be inhibited. There are reports that lactobacilli produce components which inhibit attachment of enterotoxigenic *Escherichia coli* to intestinal mucosa. In addition, various compounds produced during growth of the probiotic have been shown to inhibit pathogen growth. These include organic acids such as lactic and acetic acid, reuterin and bacteriocins. Organic acids lower the pH and thereby can indirectly affect growth of the pathogen. In addition, the lactic and acetic acids can be toxic to microbes. Reuterin which inhibits the growth of a very broad range of cells is produced by *Lactobacillus reuteri* when grown in the presence of glycerol. Numerous bacteriocins have been reported to be produced by lactobacilli e.g. Acidophilin, Acidolin, Lactocidin, Bacteriocin, Bulgarican, Lactolin, Lactobacillin and Lactobrevin. They can either have a very broad range of activity or alternatively specifically inhibit the growth of a very limited range of closely related microbes. For example, Lactobacillus sp can exhibit specific antagonistic effects towards *Clostridium ramnosum*.

There are different levels of specific bacterial populations in the various regions of the gastrointestinal tract of humans and animals. In addition, it has been shown that the specific strains of the various genera and species vary from one region of the digestive tract to another. It has been shown that dietary fibre influences microbial activity and gas production in the various regions of the gastrointestinal tract of pigs.

In humans it is known that the major carbohydrate sources for bacterial growth in the colon are provided by dietary and endogenous means and that bacteria in the proximal colon have a relatively high supply of dietary nutrients and grow at a fast rate causing a decrease in nutrients available in the distal region resulting in bacteria growing more slowly and the pH frequently approaches neutrality. Because of these varying physiochemical conditions, gross metabolic differences are likely to occur between bacteria resident in the right or left sides of the colon. There is a correlation between the fast and slow rate of bacterial growth in the proximal and distal colon, respectively, with the incidence of disease, including cancer. In the region of fast growth, there is a lower incidence of disease than in the distal colon.

It is the contention of many scientists that the health and well being of people can be positively or negatively influenced by the microorganisms which inhabit the gastrointestinal tract, and in particular, the large bowel. These microorganisms through the production of toxins, metabolic by-products, short chain fatty acids, and the like affect the physiological condition of the host.

The constitution and quantity of the gut microflora can be influenced by conditions or stress induced by disease, life style, travel, and other factors. If microorganisms which positively affect the health and well being of the individual can be encouraged to populate the large bowel, this should improve the physiological well being of the host.

The introduction of beneficial microorganisms, or probiotics, is normally accomplished by the ingestion of the organisms in drinks, yoghurts, capsules, and other forms in such a way that the organism arrives in a viable condition in the large bowel.

It has been demonstrated by Englyst H. N. et al (1987) "Polysaccharides breakdown by mixed populations of human faecal bacteria", FEMS Microbiology Ecol 95: 163–71, that the bacterial fermentation of resistant starch in the large bowel produces elevated levels of short chain fatty acids, particularly beneficial types such as propionate and butyrate.

The present inventors have realised that it would be desirable to not only deliver probiotic microorganisms to the large bowel but also to provide a medium that would function to promote the growth of the microorganisms when they reach the large bowel.

Surprisingly, it has been found that modified or unmodified resistant starches may function both as a means to transport the probiotic microorganisms to the large bowel and as a growth medium for the microorganism delivered to the target region of the large bowel. It has also been shown in International publication number WO 96/08261, the content of which is incorporated into this specification for the purposes of convenient cross-reference, that resistant starch may be eroded or pitted to afford protection of the associated probiotic microorganisms and that the microorganisms may also adhere to these starch granules. There is a need, however, to be able to deliver probiotics in a more efficient and economical manner.

It would also be desirable to be able to deliver substrate to specific sites of the gastrointestinal tract so as to either enhance or suppress the growth of particular populations of microorganisms at those sites without substantially affecting the populations of other microorganisms at other sites. The present inventors have developed improved methods for altering or influencing microbial populations of the gastrointestinal tract of animals including humans.

DISCLOSURE OF INVENTION

In a first aspect, the present invention consists in a method of enhancing a resident population of microorganism in a selected site of the gastrointestinal tract of an animal, the method comprising providing to the animal a selected modified or unmodified resistant starch or mixtures thereof in combination with one or more probiotic microorganisms such that upon ingestion the starch passes through the gastrointestinal tract substantially unutilized until it reaches the selected site where it is utilised by the resident and/or the probiotic microorganisms thereof causing an increase in number and/or activity of the microorganisms.

In a second aspect, the present invention consists in a method of suppressing an undesired resident population of microorganism in a selected site of the gastrointestinal tract of an animal, the method comprising providing to the animal a modified or unmodified resistant starch or mixtures thereof in combination with one or more probiotic microorganisms such that upon ingestion the starch passes through the gastrointestinal tract substantially unutilized until it reaches the selected site where it is utilised by another resident and/or the probiotic microorganisms causing an increase in number and/or activity of the other microorganisms and suppressing the growth and/or activity of the undesired microorganism.

By selecting a resistant starch or a specific modification of resistant starch in combination with a probiotic preparation of one or more microorganisms, it is possible to deliver substrates which are more poorly used by the microorganisms of one part of the colon than another part. For example, the microorganisms in the proximal colon may poorly utilise the resistant starch selected than those microorganisms in the distal colon. Similarly, it is possible to cause one population of microorganism at a specific site of the gastrointestinal tract to grow while the remaining resident populations remain static or are suppressed by the increased growth or activity of the selected population and/or the probiotic microorganisms.

The present invention can also be used to promote growth of desirable probiotic and/or indigenous microbes in the small intestine or stomach where the levels of indigenous organisms are lower and pathogens frequently establish e.g. *H. pylori* in the stomach or enterotoxigenic *Escherichia coli* in the small intestine.

In a third aspect, the present invention consists in a method of suppressing a microbial pathogen in the gastrointestinal tract of an animal comprising administering to the animal one or more probiotic microorganisms and a carrier which will function to transport the one or more probiotic microorganisms to the large bowel or other regions of the gastrointestinal tract, the carrier comprising a modified or unmodified resistant starch or mixtures thereof, which carrier acts as a growth or maintenance medium for the non-pathogenic microorganisms in the large bowel or other regions of the gastrointestinal tract to an extent sufficient to suppress growth and/or activity of the microbial pathogen.

In a fourth aspect, the present invention consists in an improved probiotic composition comprising one or more probiotic microorganisms and a carrier which will function to transport the one or more probiotic microorganisms to the large bowel or other regions of the gastrointestinal tract, the carrier comprising modified or unmodified resistant starch or mixtures thereof to which the probiotic microorganisms are bound in a manner so as to protect the microorganisms during passage to the large bowel or other regions of the gastrointestinal tract, which carrier acts as a growth or maintenance medium for microorganisms in the large bowel or other regions of the gastrointestinal tract.

In a fifth aspect, the present invention is directed to an improved method of providing probiotic microorganisms to the gastrointestinal tract of an animal, the improved method comprising administering to the animal one or more probiotic microorganisms and a carrier which will function to transport the one or more probiotic microorganisms to the large bowel or other regions of the gastrointestinal tract, the carrier comprising modified or unmodified resistant starch or mixtures thereof to which the probiotic microorganisms are bound in a manner so as to protect the microorganisms during passage to the large bowel or other regions of the gastrointestinal tract, which carrier acts as a growth or maintenance medium for microorganisms in the large bowel or other regions of the gastrointestinal tract.

In a preferred form, the probiotic microorganisms are bound irreversibly to the modified or unmodified resistant starch.

In a sixth aspect, the present invention consists in a method of reducing the incidence of colorectal cancer or colonic atrophy in an animal, the method comprising providing to the animal one or more SCFA producing probiotic microorganisms and a carrier which will function to transport the one or more probiotic microorganisms to the large bowel or other regions of the gastrointestinal tract, the carrier comprising a modified or unmodified resistant starch or mixtures thereof, which carrier acts as a growth or maintenance medium for microorganisms in the large bowel or other regions of the gastrointestinal tract so as to enhance SCFA production by probiotic and/or resident microorganisms in the gastrointestinal tract of the animal.

In a preferred form of the present invention, the SCFA is butyrate and the microorganisms in the gastrointestinal tract are *Cl. butyricum* and/or Eubacterium. In order to further enhance the levels of SCFA, the probiotic composition includes *Cl. butyricum* and/or Eubacterium.

It will be appreciated that the modified or unmodified resistant starch or mixtures thereof may also act as a growth or maintenance medium for microorganisms in the large bowel or other regions of the gastrointestinal tract so as to enhance short chain fatty acid (SCFA) production by microorganisms in the gastrointestinal tract of the animal.

As used in this specification, "resistant starch" includes those forms defined as RS1, RS2, RS3 and RS4 as defined in Brown, McNaught and Moloney (1995) Food Australia 47: 272–275. Either modified or unmodified resistant starches or mixtures thereof are used in this invention. The advantage of selected resistant starches is that they are not digested until they reach the selected site of gastrointestinal tract. Therefore, when used in combination with a probiotic, they also provide a readily available substrate for fermentation by the probiotic microorganisms as soon as they arrive in the selected site of the gastrointestinal tract. A preferred form of resistant starch is a high amylose starch particularly high amylose starches as disclosed and taught in WO 94/03049 and WO 94/14342, the contents of which are incorporated into this specification for the purposes of convenient cross-reference.

In WO 94/03049 and WO 94/14342, high amylose starches are disclosed which are resistant starches and include maize starch having an amylose content of 50% w/w or more, particularly 80% w/w or more, rice and wheat starch having an amylose content of 27% w/w or more and: particular granular size ranges of starches having an amylose content of 50% or more and enhanced resistant starch content, these starches including maize. barley, wheat and legumes. This invention is not, however, limited to use of these forms of resistant starch. For example, other forms of resistant starch are derived from sources such as bananas, fruits and potatoes.

It may be advantageous to also chemically modify the starch to, for instance, alter the charge density or hydrophobicity of the granule and/or granule surface to enhance the attachment compatibility between the microorganism and the resistant starch. Chemical modifications, such as etherification, esterification, acidification and the like are well known in this art as being suitable chemical treatments. Similarly other modifications can be induced physically, enzymically or by other means known to the art.

It may also be useful to modify the degree of enzyme susceptibility of the resistant starch by altering the conformation or structure of the starch. Examples include acid or enzyme thinning and cross bonding using difunctional reagents.

One useful modification is the amylolysis of high amylose starches to give starch granules characterised by pits or erosions which can extend from the surface to the interior of the granules. These pits allow the entry of enzymes to the more enzyme susceptible core of the starch granule which is solubilised.

As used herein, Hi-maize™ (trade mark) refers to a high amylose starch obtained from Starch Australasia Limited.

In order that the present invention may be more clearly understood, preferred forms thereof will be described with reference to the following figures and examples.

MODES FOR CARRYING OUT THE INVENTION

EXAMPLE 1

Figure 1:
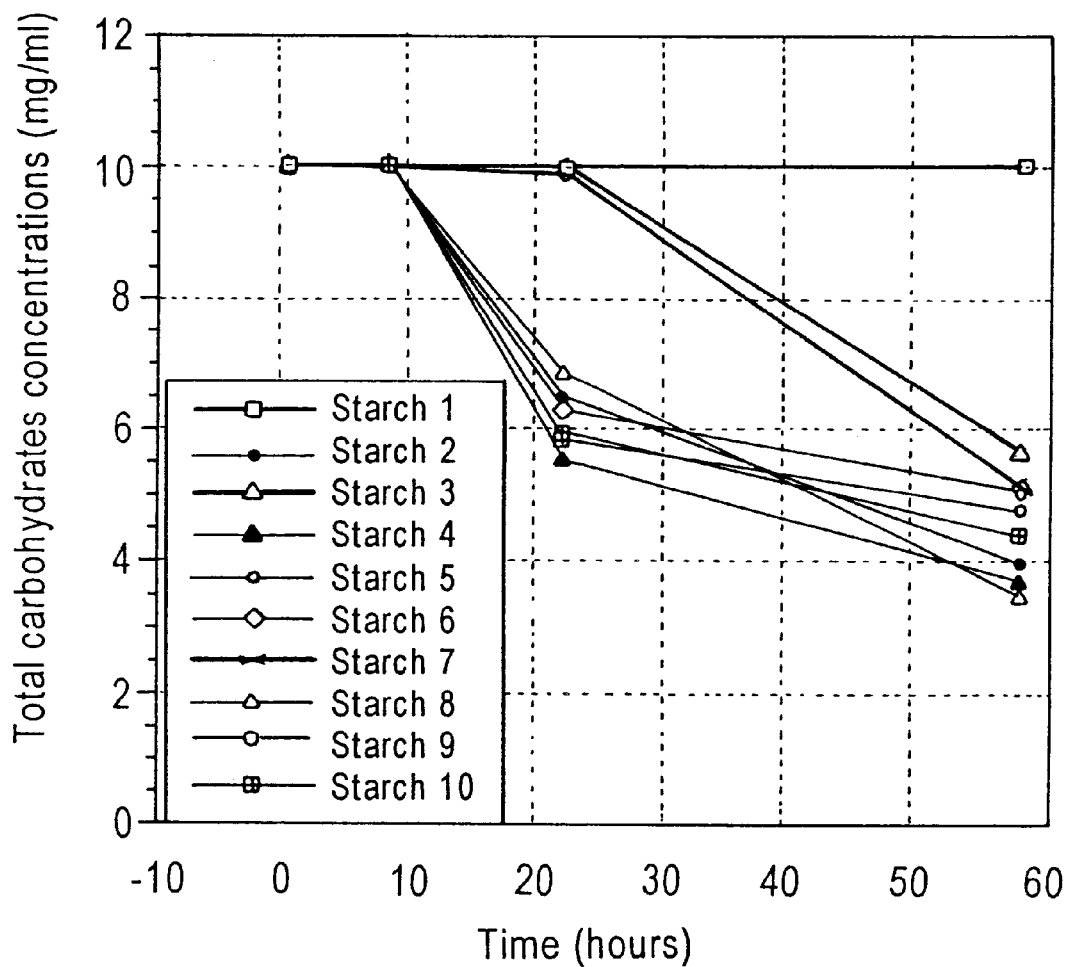
FIG. 1 shows utilazation of of starches 1–10 by Bifiobacterium strain X8AT2.
Figure 2:
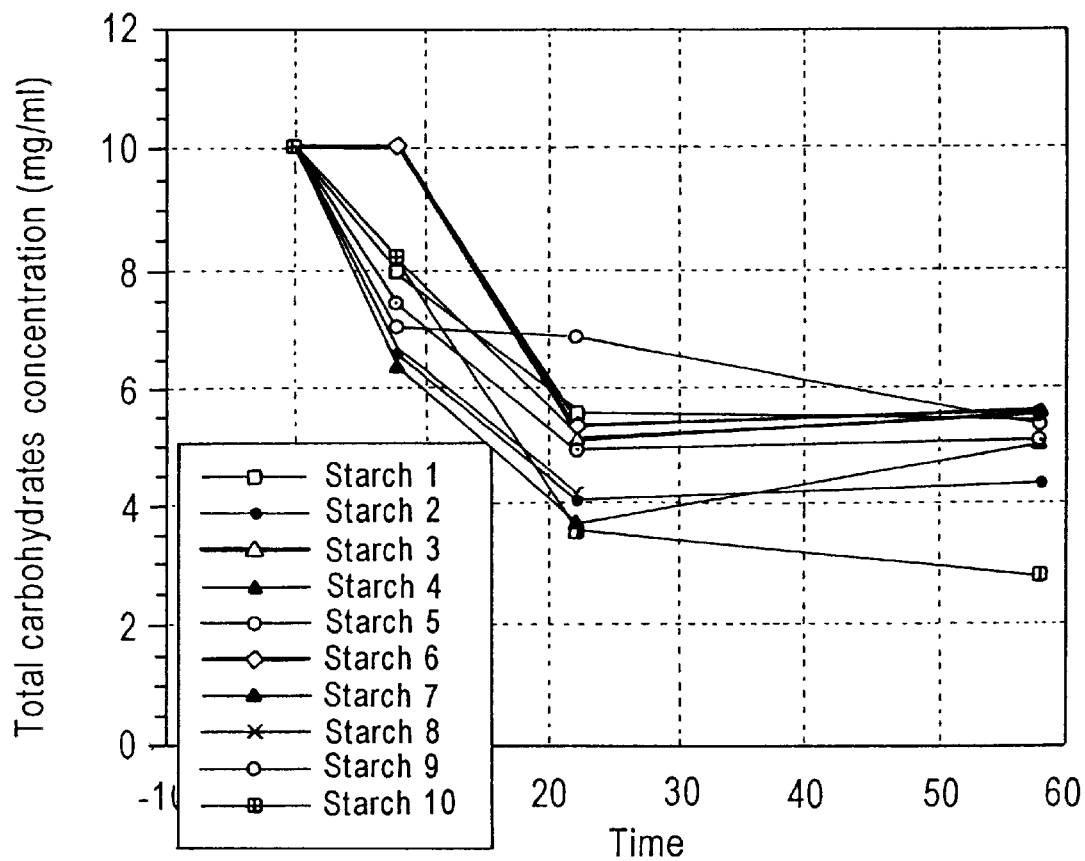
FIG. 2 shows utilisation of starches 1–10 by of *Bif. pseudolongum;*
Figure 3:
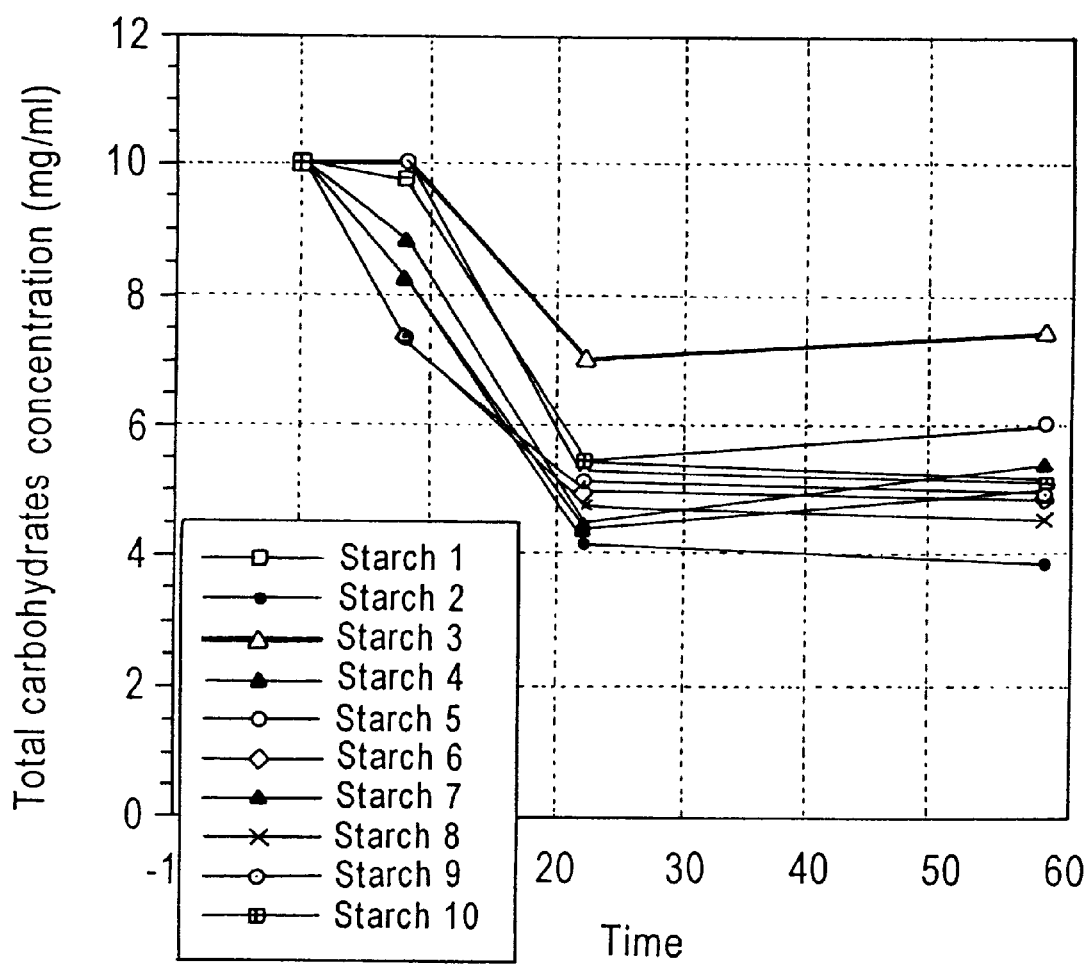
FIG. 3 shows utilisation of starches 1–10 by *Bif. bifidum;*
Figure 4:
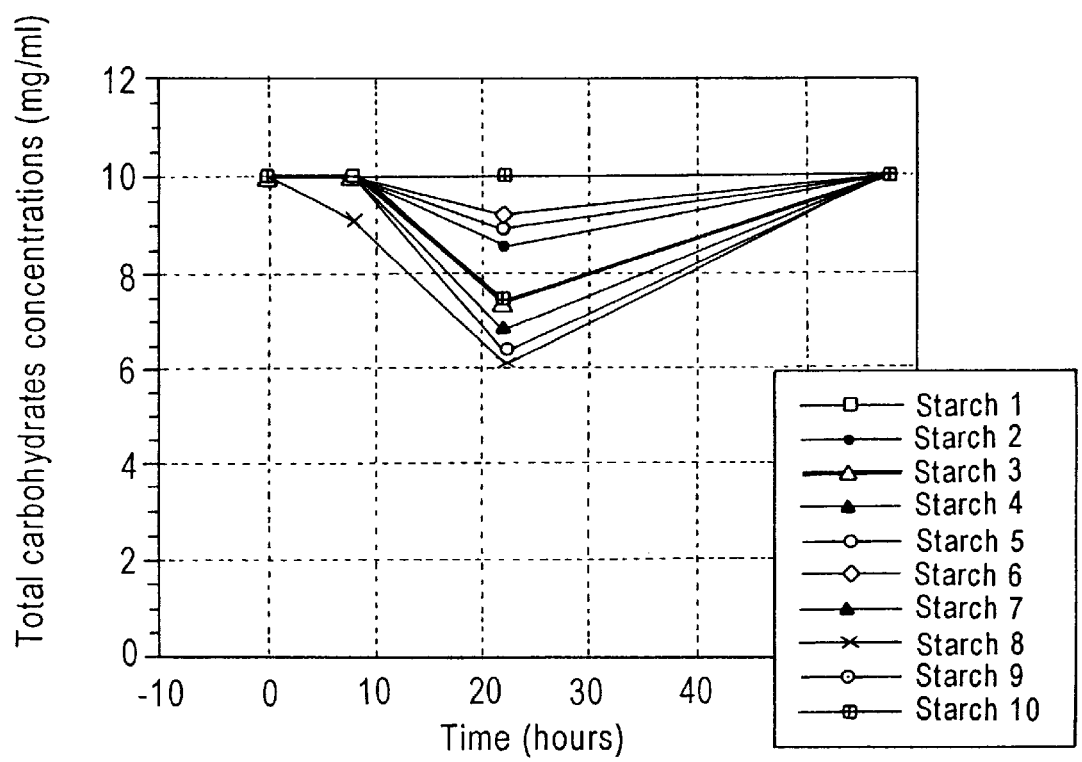
FIG. 4 shows utilisation of starches 1–10 by *Bact. vulgatus;*
Figure 5:
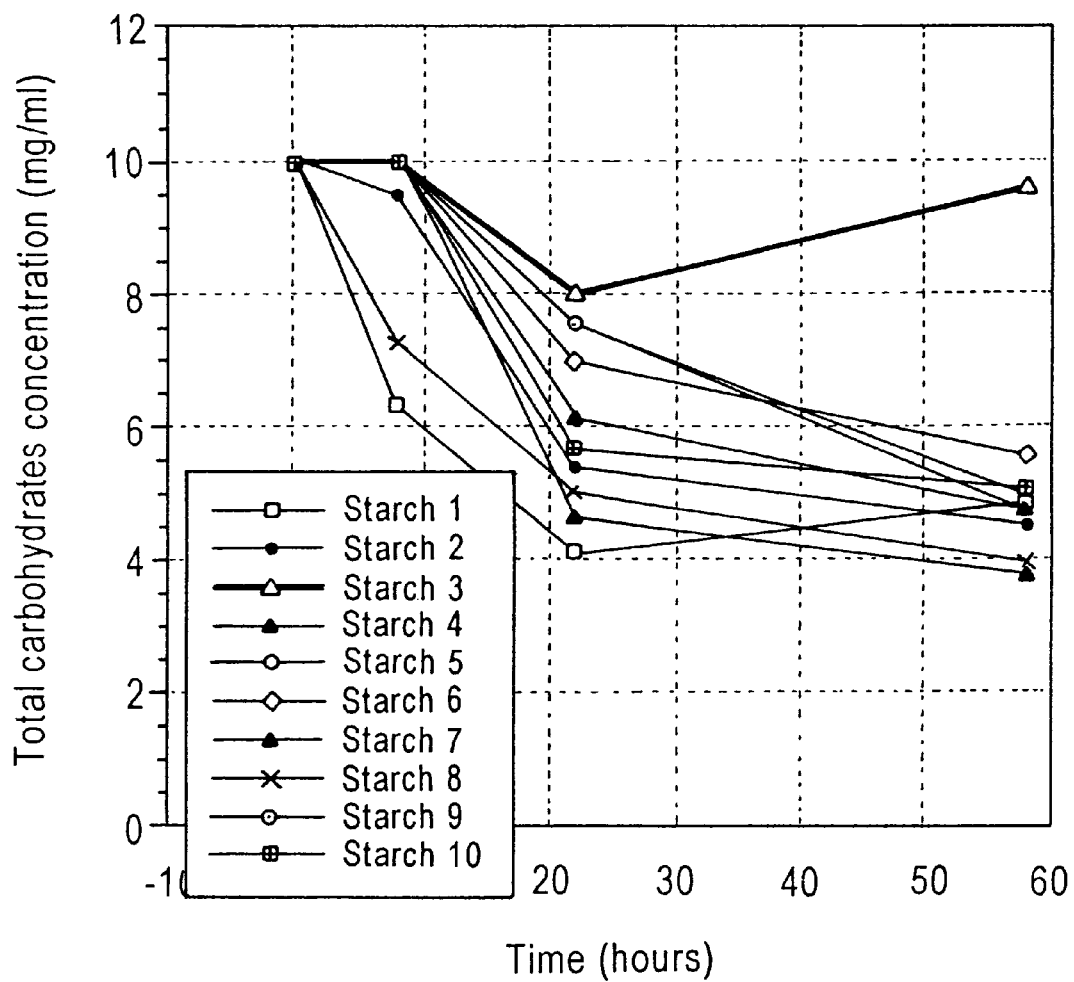
FIG. 5 shows utilisation of starches 1–10 by Bact. fragilis.
Figure 6:
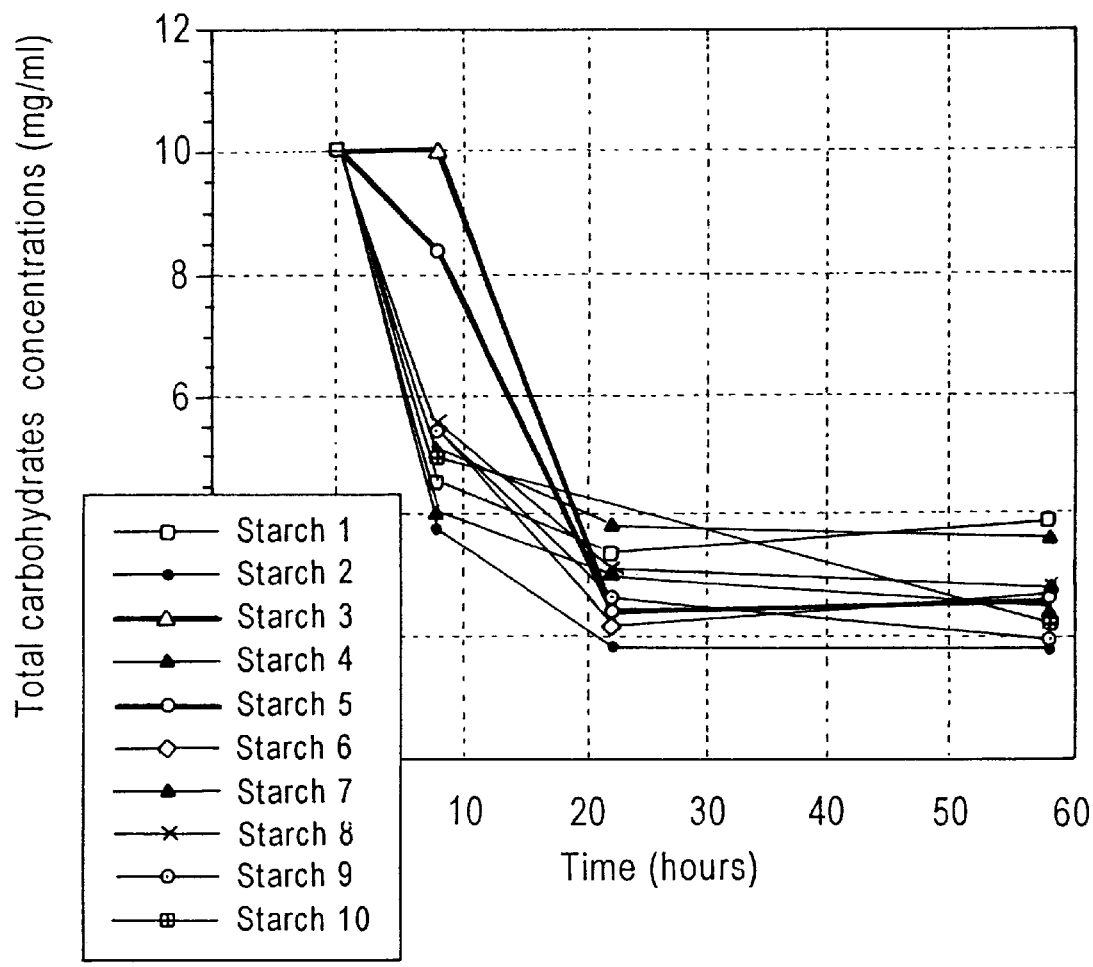
FIG. 6 shows utilisation of starches 1–10 by *Cl. butyricum;*

A defined growth medium described in Table 1 was prepared containing Hi-maize™ starch and modifications thereof, and after inoculation, the total carbohydrate concentration was determined in the growth medium at 0, 8, 22, and 58 hours. The various starches use are shown in Table 2. As can be seen in FIGS. 1–6 some modifications were favoured by some strains more than others e.g. starches 1 and 8 were clearly more favourable for growth of *B. fragilis* (FIG. 5) and while starches 3 and 5 were utilised by *Clostridium butyricum,* the consumption was slow relative to starch 2 (FIG. 6). FIGS. 1, 2 and 3 show variability between the individual species of Bifidobacterium with some starches being rapidly consumed by one strain and not by another, while some starches are not consumed well by any Bifidobacterium e.g. starch 3.

TABLE 1

Composition of medium used for growing intestinal strains of bacteria.

| Ingredient | Amount |
| --- | --- |
| Bacteriological peptone | 7.5 g |
| Yeast extract | 2.5 g |
| Tryptone | 5.0 g |
| Starch | 10.0 g |
| $K_2HPO_4$ | 2.0 g |
| $KH_2PO_4$ | 1.0 g |
| $NaHCO_3$ | 0.2 g |
| $NaCl_2$ | 2.0 g |
| $MgCl_2$ | 0.2 |
| $CaCl_2$ | 0.2 g |
| $MnCl_2$ | 0.02 g |
| $CoCl_2$ | 0.02 g |
| Cystein | 0.5 g |
| $FeSO_4$ | 0.005 g |
| Tween 80 | 2 ml |
| Hemin | 0.005 g |
| Vit $B_{12}$ | 0.001 g |
| Vit K | 0.0005 g |
| Water (final volume) | 1 liter |

TABLE 2

Starch identification

| Starch | Destination | Identification | Analysis |
| --- | --- | --- | --- |
| 1 | A939 (D19) | Hydroxypropylated | DS* = 0.13 |
| 2 | A938 (C79) | Acetylated | Acetyl value = 2.69% |
| 3 | A961 (D8) | Octenyl succinated | OSA value = 4.73% |
| 4 | A955 (D2) | Carboxymethylated | Carboxyl value = 1.0% |
| 5 | A960 (D7) | Succinated | Succinyl value = 3.97% |
| 6 | HA 008 (D2118) | Unmodified | — |
| 7 | A993 D42 | Succinated | Succinyl value = 4.1% |
| 8 | A956 (D1) | Carboxymethylated | Carboxyl value = 2.0% |
| 9 | A995 (D57) | Acetylated | Acetyl value = 4.0% |
| 10 | A965 (D9) | Hydroxypropylated | DS = 0.13 |

*degree of substitution

TABLE 3

Comparison of starch utilisation rates (0–8 hours and 8–22 hours)

| Bacteria | _____ Starches _____ | | | | | | | | | |
|---|---|---|---|---|---|---|---|---|---|---|
| | 1 | 2 | 3 | 4 | 5 | 6 | 7 | 8 | 9 | 10 |
| Cl. butyricum | 0.682 | 0.780 | 0.000 | 0.610 | 0.203 | 0.574 | 0.741 | 0.562 | 0.574 | 0.633 |
| | 0.084 | 0.138 | 0.546 | 0.092 | 0.426 | 0.231 | 0.078 | 0.170 | 0.197 | 0.353 |
| Bif. psuedolongum | 0.259 | 0.431 | 0.000 | 0.454 | 0.371 | 0.003 | 0.227 | 0.415 | 0.323 | 0.394 |
| | 0.171 | 0.180 | 0.351 | 0.193 | 0.014 | 0.333 | 0.218 | 0.180 | 0.180 | 0.157 |
| Bif. bifidum | 0.000 | 0.227 | 0.000 | 0.147 | 0.000 | 0.339 | 0.219 | 0.339 | 0.000 | 0.035 |
| | 0.340 | 0.290 | 03212 | 0.309 | 0.326 | 0.167 | 03277 | 0.184 | 0.351 | 0.308 |
| Bact. fragilis | 0.463 | 0.057 | 0.000 | 0.000 | 0.000 | 0.000 | 0.000 | 0.347 | 0.000 | 0.000 |
| | 0.159 | 0.292 | 0.143 | 0.381 | 03175 | 0.216 | 0.276 | 0.159 | 0.175 | 0.310 |
| Bact. vulgatus | 0.000 | 0.000 | 0.000 | 0.000 | 0.000 | 0.000 | 0.000 | 0.115 | 0.000 | 0.000 |
| | — | 0.102 | 0.184 | 0.225 | 0.075 | 0.056 | 0.035 | 0.212 | 0.262 | 0.221 |
| X8AT2 | 0.000 | 0.000 | 0.000 | 0.000 | 0.000 | 0.000 | 0.000 | 0.000 | 0.000 | 0.000 |
| | 0.008 | 0.251 | 0.000 | 0.319 | 0.267 | 0.148 | 0.011 | 0.225 | 0.299 | 0.291 |

When the rate of utilisation of the starch between 0 and 8 hours and between 8 and 22 hours was estimated it was seen that some starches were used more rapidly than others by specific bacteria of intestinal origin (Table 3).

It is therefore apparent that one can tailor make a starch to selectively enhance bacteria at specific sites in the gastrointestinal tract. This can be applied both to enhance indigenous bacteria as well as probiotic bacteria which can be dosed together with the starch, or either before or after the starch. Since different regions in the gastrointestinal tract can be, or are already, colonised by different genera of bacteria or different species or strains of the same species, it is therefore possible to manipulate site or region specific microbial growth in the gastrointestinal tract of man and animals. This can be of value in several disease situations in which it would be desirable to suppress microbial growth of undesirable microbes e.g. diarrhoea or bacterial overgrowth, or desirable to enhance growth of beneficial ones e.g. Cl. butyricum in the distal bowel and thereby raise levels of butyrate and reduce the risk of colon cancer and atrophy of the epithelial mucosa.

One can demonstrate these parameters initially using cultures of faecal slurries, a rodent model or pigs since the various sites of the gut can be sampled. There are already available a number of animal models to allow one to study the various disease conditions described below to which this invention can be applied.

Uses

Control of site specific bacterial fermentation in the intestine;

Reduced colon cancer risk by enhancing fermentation in lower regions of the intestine;

Prophylactic or therapeutic control of bacterial overgrowth since can target the site of overgrowth with specific probiotic strain and the appropriately modified resistant starch which can be selectively utilised by that strain; and Modifications of resistant starch can be used alone or in combination with a probiotic or mixtures of probiotic strains to manipulate microbial growth at particular sites. This can be applied to disease conditions such as constipation, diarrhoea, irritable bowel syndrome, ulcerative colitis, inflammatory bowel disease, Crohns disease, as well as gastric and duodenal ulcers and cancer.

Methods

Investigation of antagonist effects of human isolates of Bifidobacterium X8AT2 and X13AT2, with/without *Lactobacillus fermentum* KLD or *Lactobacillus acidophilus*, against *S. typhimurium* and *E. coli* in the serum tubes with medium which contained different starches.

Experimental Procedure

Stationary phase cultures of *Lact. acidophilus* or *Lact. fermentum* were grown overnight in MRS, *S. typhimurium* grown in TSB broth (plus 5 mg/ml streptomycin sulfate), *E. coli* grown in MacConkeys broth, and Bif. X8AT2 or X13AT2 grown in PYG innoculated into anaerobic serum tubes containing 20 ml of test medium (Table 1). The basic composition of medium is identical to the amylose medium with individual starches (1%) used as the sole carbon source. Starches used here include 10 different starches from Goodman Fielder Company, and amylose, amylopectin from Sigma Chemical Company and soluble starch from BDH. Starches from Goodmen Fielder Company are shown in Table 2.

Inoculation. The serum tubes were divided into three groups:

Group (1) added 1 ml Bifidobacterium cultures+1 ml Lactobacillus cultures, and then 0.1 ml cultures of *S. Typhimurium* and 0.1 ml *E. coli* which has been diluted ×10$^4$ with TSB and MacConkey respectively.

Group (2) 1 ml Bifidobacterium cultures, plus 0.1 ml diluted *S. typhimurium* and *E. coli* respectively.

Figure 7:
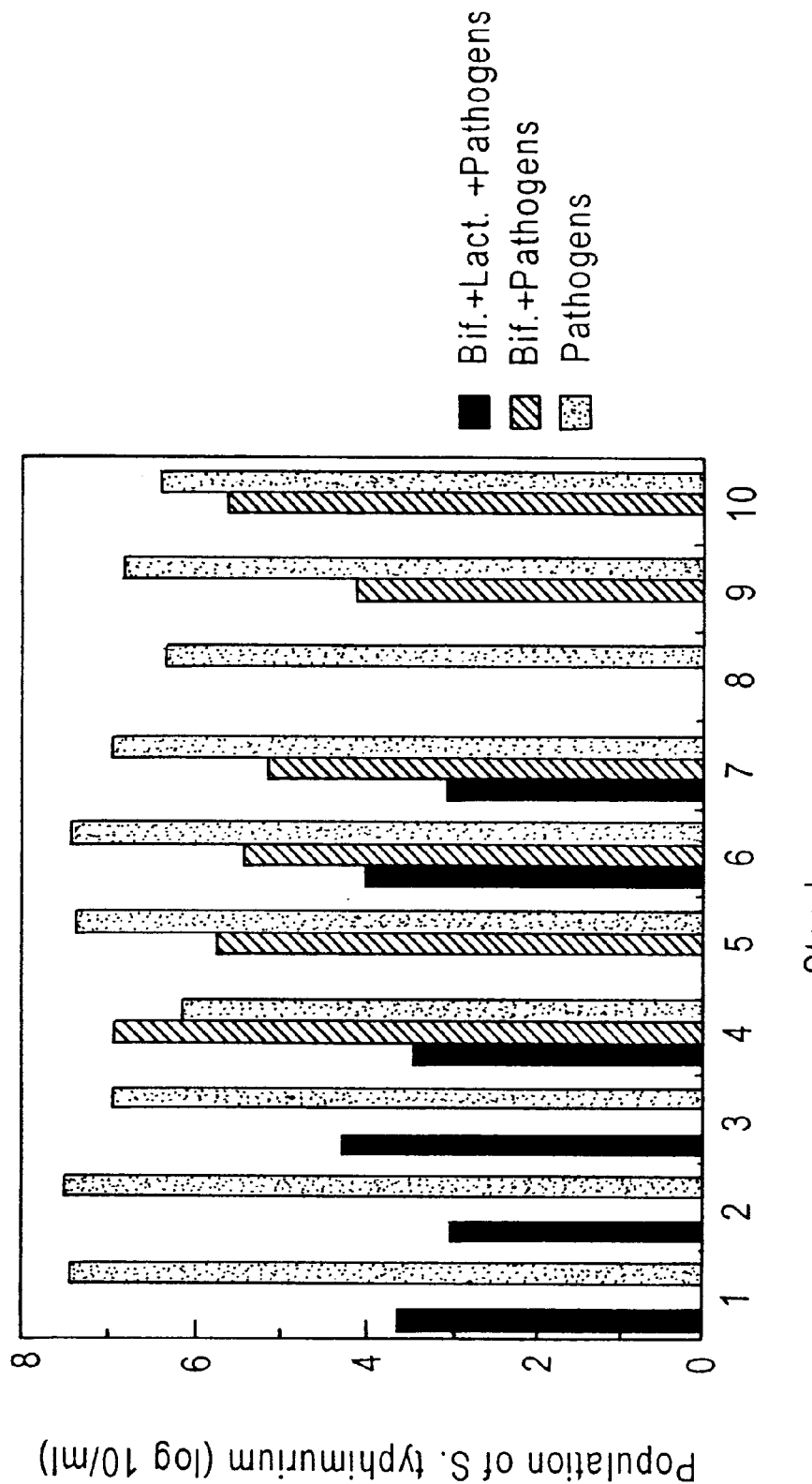
FIG. 7 shows *Salmonella typhimurium* in cultures 24 h post inoculation with Bif X13AT2 and *Lactobacillus acidophilus;*
Figure 8:
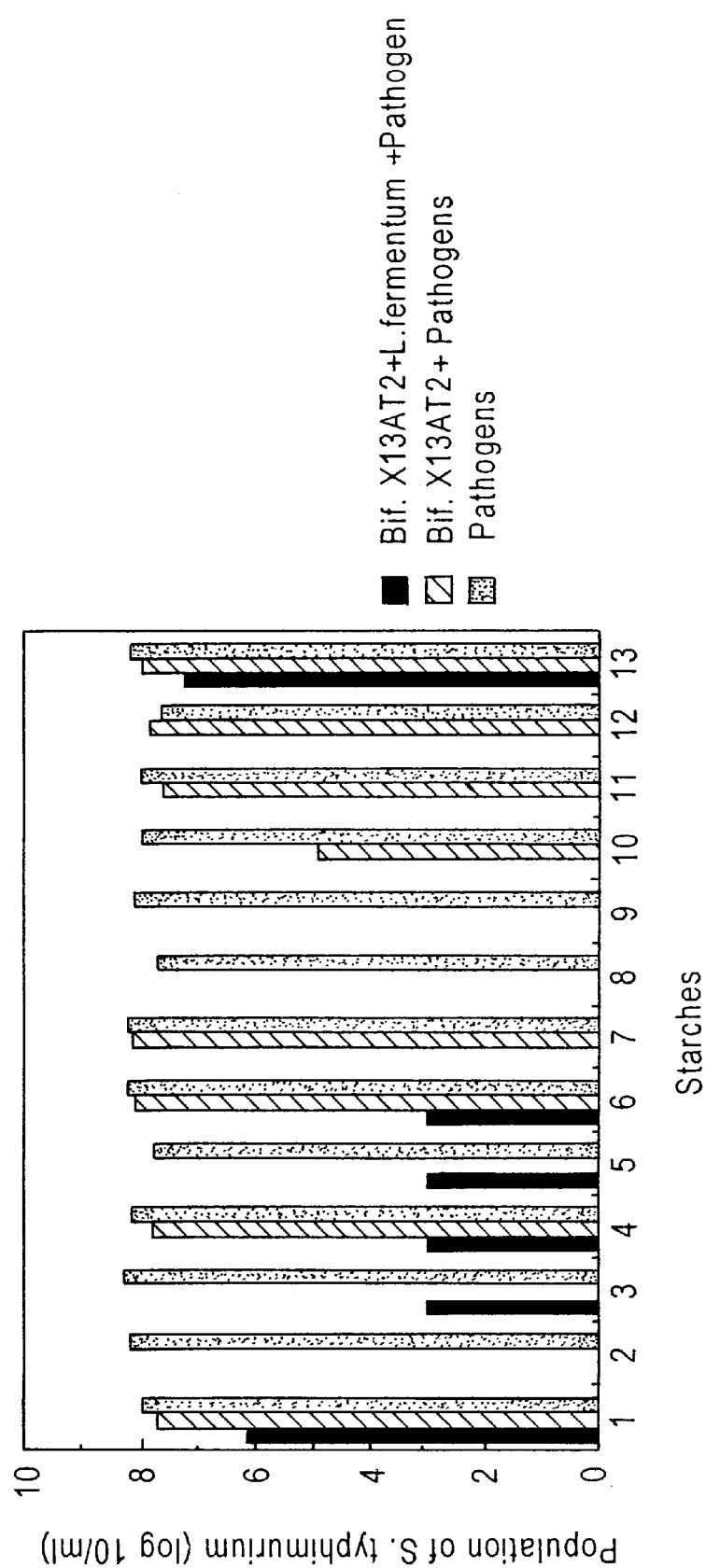
FIG. 8 shows *Salmonella typhimurium* in cultures 24 h post inoculation with Bif X13AT2 and Lactobacillus spp.

Viable Salmonella were enumerated after 24 h fermentation. As can be seen in FIGS. 7 and 8, some starces, namely 8 and 10, induced a reduction in Salmonella when Bifidobacterium and Lactobacillus were combined. This synergistic effect with the mixture of bifidobacterium and Lactobacillus will provide an enhanced method of pathogen inhibition.

EXAMPLE 2

Figure 9A:
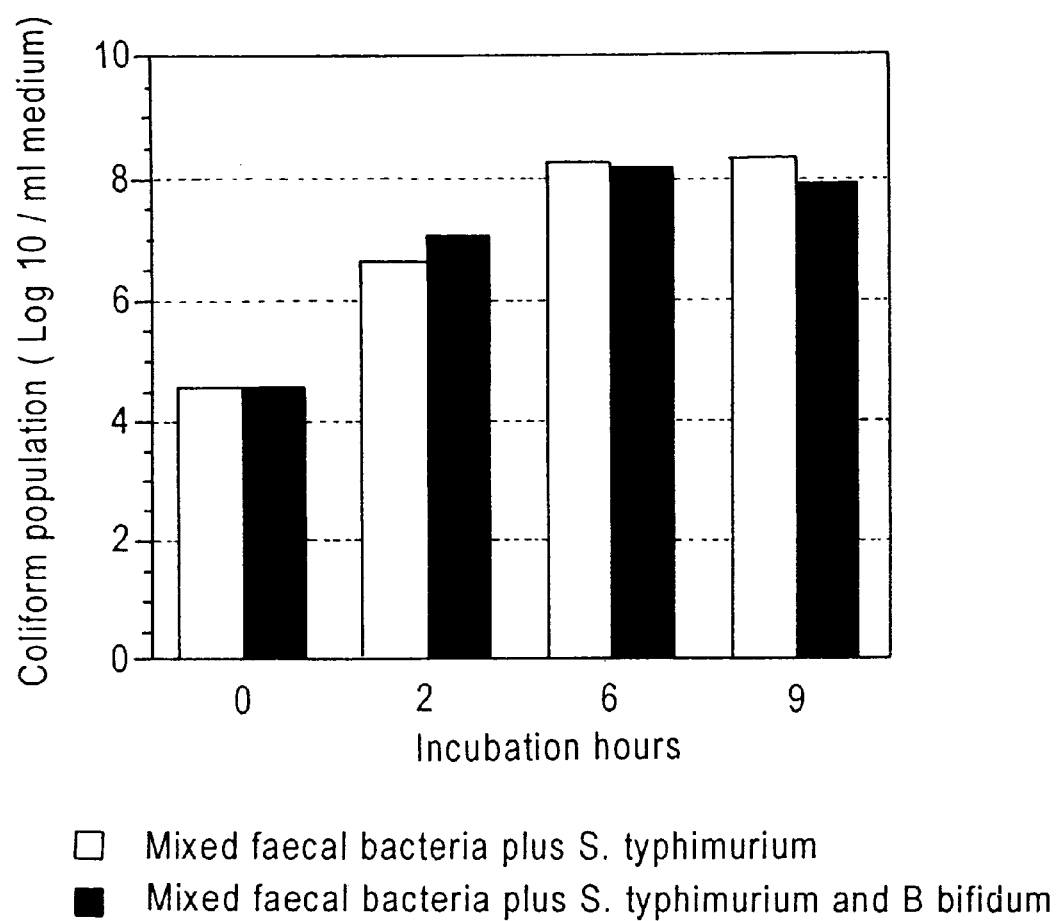
FIG. 9 shows Coliform populations.
Figure 9B:
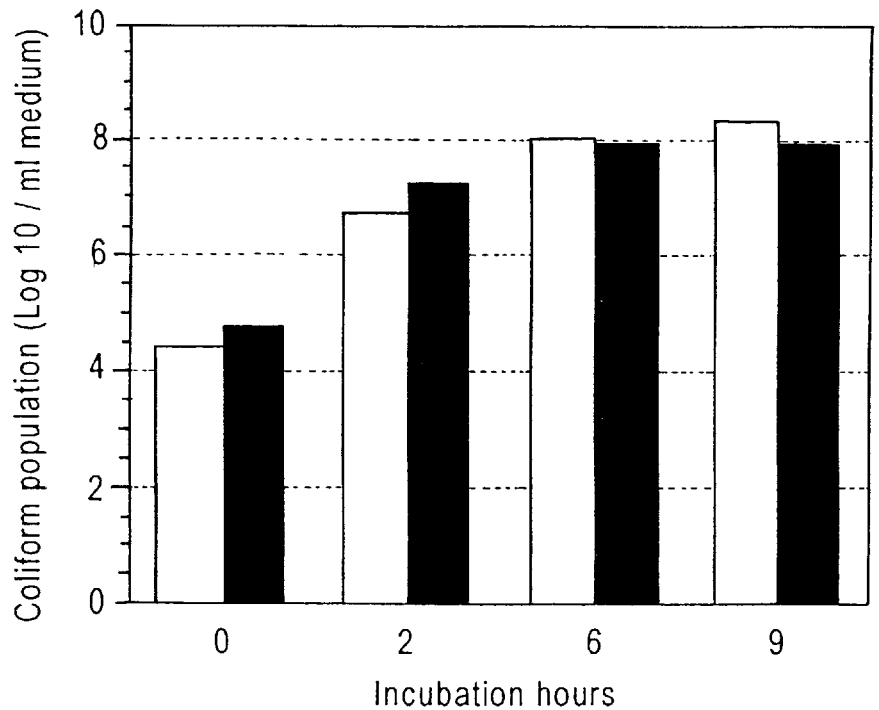
Figure 9C:
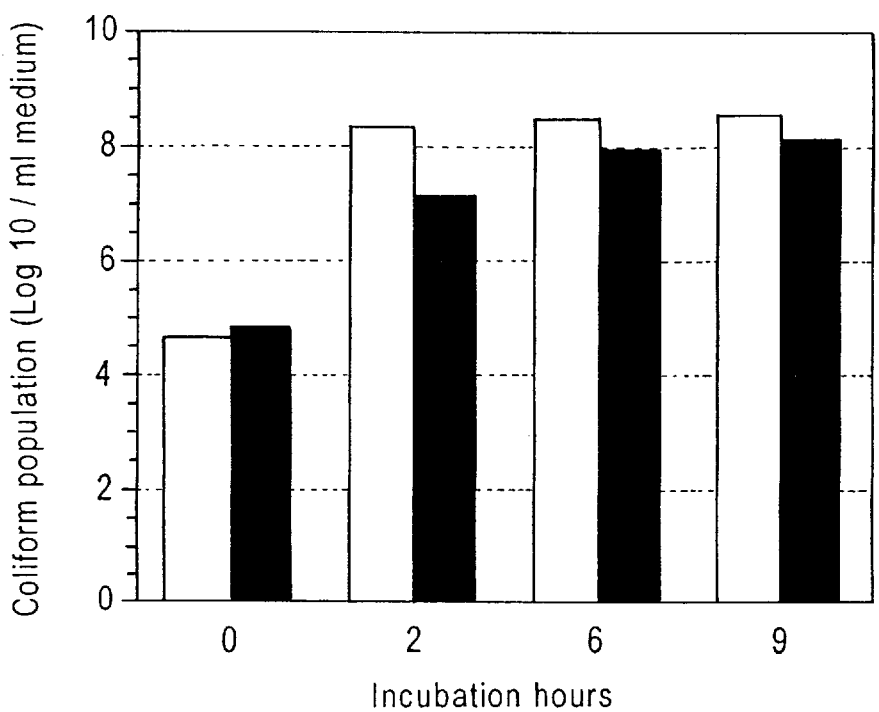
Figure 10:
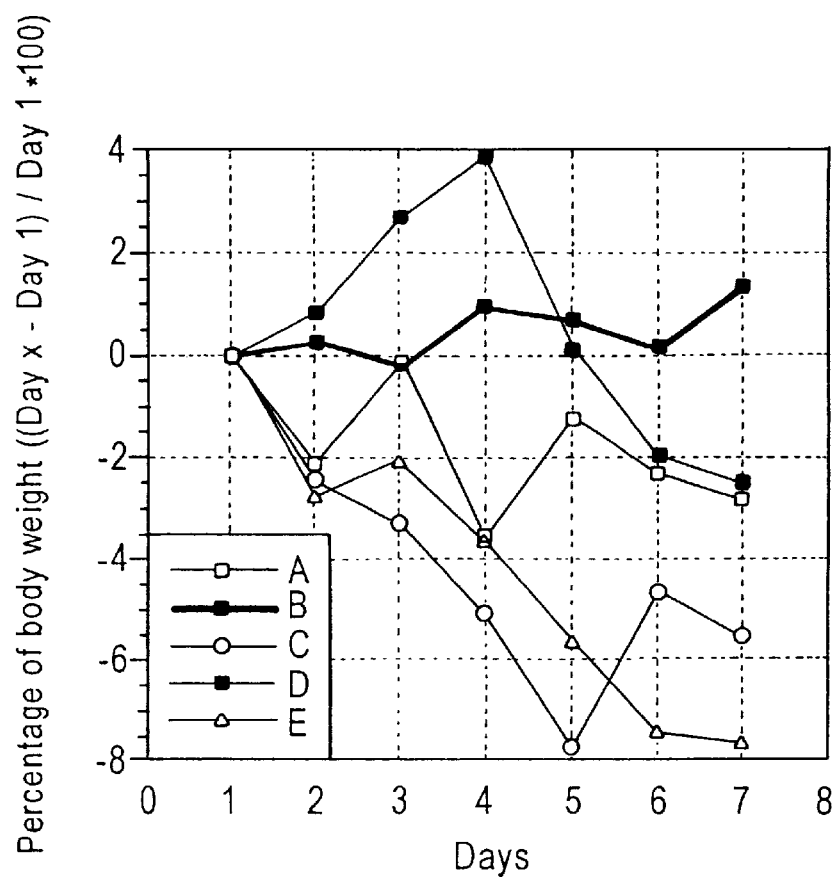
FIG. 10 shows weight of mice.

The effect of a number of probiotic compositions has been studied by enumerating coliforms and salmonella in vitro in the presence of resistant starch and modifications of resistant starch singly or together with bifidobacteria when the system has been challenged with Salmonella. More specifically, aliquots (1 ml) of human faecal homogenates (10 g per 100 ml diluent) were added to diluted WC broth (diluted 50:50 with 0.05M phosphate buffer) to which were added the resistant starch and modifications thereof referred to as Starches 1 to 10. For each of the starches, parallel tubes were prepared with one set being inoculated with various Bifidobacterium spp. All mixtures were then inoculated with salmonella and sampled after 0, 2, 6 and 9 hours incubation. Results are expressed as the numbers of coliforms when enumerated as colony forming units per ml using MacConkey No 1 agar (FIGS. 9*a*, *b* and *c*). It can be seen that when resistant starch (FIG. 9) is added together with bifidobacteria, the numbers of coliforms are reduced compared to the starch alone. Furthermore, this effect is enhanced by modifications of the resistant starch as seen in FIG. 10 and FIG. 9c for A955 and A960, with these corresponding to carboxymethylated and succinated resistant starch, respectively. The individual modifications exert altered enhancement.

EXAMPLE 3

In addition to studying a reduction in coliform numbers as indicators of pathogens, an effect of a pathogen on the host has been studied in viva in the presence of resistant starch and modifications of resistant starch singly or together with bifidobacteria when the system has been challenged with salmonella. The parameter investigated was weight loss after salmonella administration. The experimental design is as follows: Mice were fed a defined diet (Table 4) and groups A, B, C and E were orally dosed with bifidobacteria (200 microliter per day). All groups received a single oral dose of Salmonella sp (0.1 ml containing about log 8 viable cells) and were monitored daily for weight lose.

TABLE 4

Diets for mice probiotic feeding experiments.

| Test Groups | A | B | C | D | E |
|---|---|---|---|---|---|
| Starch | Waxy | HA | Carboxy-methyl | HA | None |
|  | 400 | 400 | 400 | 400 |  |
| Casein | 200 | 200 | 200 | 200 |  |
| Canola oil | 25 | 25 | 25 | 25 |  |
| Sunflower oil | 25 | 25 | 25 | 25 |  |
| Sucrose | 150 | 150 | 150 | 150 |  |
| Wheat bran | 100 | 100 | 100 | 100 |  |
| Gelatin | 20 | 20 | 20 | 20 |  |
| Mineral mix | 67 | 67 | 67 | 67 |  |
| Vitamin mix | 13 | 13 | 13 | 13 |  |
| Methionine | 2 | 2 | 2 | 2 |  |
| Bacterial strain | X8AT2 | X8AT2 | X8AT2 | None | X8AT2 |

Waxy = waxy maize; HA = High amylose starch; Carboxy-methyl = Carboxymethylated high amylose starch. All weights are in grams. Bacterial cultures (100 microliters per day) were orally ingested by the mice with starch containing meals.

Results are presented in FIG. 10 and show that the combined dosage of resistant starch and bifidobacteria prevented the weight loss induced by oral administration of salmonella. This effect was affected by the particular modification of the resistant starch since the modification tested, namely carboxymethylated, had a marked detrimental effect. Interestingly, the resistant starch in the absence of the bifidobacteria had an initial positive effect after which the weight loss was more rapid.

Uses

The present invention can be applied to all conditions in which pathogens have been identified or proposed as causative agents of intestinal disease in both man and animals. Since infective diarrhoea has been shown to be improved by probiotic dosage, the present invention can be used to enhance the effect of the probiotic by itself. In addition, the present invention may used effectively to improve non-infective diarrhoea which has not been shown to be influenced by probiotics alone. It could also be used effectively in reducing the effects of dietary related diarrhoea problems.

Infective diarrhoea refers to all cases of diarrhoea, both acute and chronic, in which the causative agents can be shown to be microbial, including bacterial, viral and protozoan. Such infective diarrhoea can manifest itself in a number of ways e.g. (a) infantile diarrhoea which is frequently associated with viral agents and salmonella, (b) antibiotic associated diarrhoea, (c) traveller's diarrhoea.

Both prophylactic and therapeutic uses of the present method are envisaged. The former can relate to prevention when the individual can be exposed to potential problems e.g. (i) investigative gastrointestinal examination when the bowel is decontaminated and can then be recolonised by an undesirable microbial population (ii) travellers exposed to an altered pathogen load or an alteration of the gastrointestinal tract ecosystem which can predispose the individual to a lower infective dose of a pathogen. Therapeutic uses relate to the treatment of established conditions related to an undesirable balance of the gastrointestinal tract microflora or an established pathogen infection.

Enhancing production of antimicrobial substances by probiotic strains. Such antimicrobial substances can include substances which inhibit growth of a pathogen or the potential of the pathogen to colonise since pathogens frequently need to adhere as the initial step in colonisation and it has been shown that pathogen adhesion can be inhibited by metabolites of probiotic strains. The present invention will enhance these antimicrobial effects either directly or indirectly.

EXAMPLE 4

Screening the Colonic Bacteria and Probiotic Bacteria of the Adhesion to Starch Granules Adhesion test in the buffer pH 6.8

The adhesion of colonic bacterial strains and probiotic strains to amylose starch granules was detected directly by using light microscopy. The bacterial strains included Bif. X8AT1, Bif. X8AT2, Bif. X13AT2, *Bif. bifidum, Bact. vulgatus, Lact. fermentum* KLD, *Lact. casei, Lact. bulgaricus* and Lact. sp. B49. Starches used in the experiments are shown in Table 2.

Bacterial cells were collected from 2 ml overnight cultures in PYG medium be centrifuging 13,000 rpm for 5 mins. After discarding the supernatent, the pellet washed with 2 ml PBS buffer (12.1 g $K_2HPO_4$, 3.4 g $KH_2PO_4$, 85 g NaCl, dissolved in 1 L distilled water, pH 6.8), finally resuspended in 1 ml of PBS and pH 2.5 buffer. The starch solution were prepared as following: 10% of all type of starches were individually suspended in 5 ml PBS buffer. The mixtures were heated at 90° C. for 30 mins to mimic food processing procedures, then cooled down to the room temperature. A sample (0.5 ml) of each pre-cooked starch solution was mixed gently with 0.5 ml of cell suspension and incubated at 37° C. water bath for 30 mins. The supernatants were carefully removed and the pellets were washed with PBS buffer. The mixtures were set on the bench for 5 mins to precipitate the starch granules. The supernatents then were taken away to remove the reversibly bound bacteria. The numbers of bacterial adhered to starch granules were examined by phase-contact light microscopy.

Adhesion to cooked starch granules was observed with the Bif. X8AT1, X8AT2, X13AT2 and *Bif. bifidum* (Tables 5 and 6). Variation of adhesion was detected depending on the strains and starches tested. Bif. X13AT2 appeared as the best strain to bind with starch granules, but Bif. X8AT2 proved equally sufficient in the adhesion. Starch nos. 4 and 11 were the best substrates for the binding, whereas Starch nos. 1 and 3 seemed adequate.

EXAMPLE 5

See Tables 7 to 9 for results of survival of Bifidobacteriam under various cultural conditions.

EXAMPLE 6

The effect of Hi-maize in the Bifidobacterium growth medium and in the mouse diet on survival of the Bifidobacterium in vivo. Three groups of mice previously fed with normal mice diet were used. Two groups were consumed normal mouse diet and one group Hi-maize™ based diet. The composition of the Hi-maize™ diet contained (g/Kg):

| | |
|---|---|
| Hi-maize ™ starch | 400 g |
| casin | 200 g |
| canola oil | 25 g |
| sunflower oil | 25 g |
| sucrose | 150 g |
| wheat bran | 100 g |
| gelatin | 20 g |
| methorine | 5 g |
| mineral and vitamin mix | 5 g |

Two types of bacterial cultures were used in the experiments. In the first type, Bif. X8AT2 was grown in the glucose containing medium overnight, and growing Hi-maize™ containing medium was accounted as second type. The mice were housed individually during the experiment and all were orally administered with 200 ul of Bifidobacterium X8AT2 in the first hour. Group 1 were fed with normal diet dosed with 200 ul of bacteria culture previously grown in glucose, whilst the bacteria grown in Hi-maize™ starch medium were fed to the second and third groups of mice. Group 2 of mice were kept on the normal diet, group 3 mice were fed with a Hi-maize™ starch diet. All of the faecal pellets produced in the next 10 hour period after bacterial dosage were collected sequentially from individual mice and weighted immediately. The populations of Bifidobacterium X8AT2 in each faecal pellet were enumerated. The number of viable cells in the bacterial suspensions used for oral dosage were enumerated as CFU/ml. The recovery rates of Bifidobacterium X8AT2 in the three groups of mice were expressed as daily total output per mouse and as the percentage of survival in the faeces based on the numbers orrally dosed.

TABLE 5

Adhesion of human isolates and selective type strains on the modified starch granules

| Starches | 1 | 2 | 3 | 4 | 5 | 6 | 7 | 8 | 9 | 10 |
|---|---|---|---|---|---|---|---|---|---|---|
| X8AT1 | – | ± | – | +++ | + | ++ | ± | + | + | ++ |
| X8AT2 | ± | ++ | + | +++ | + | ++ | + | + | ± | ++ |
| X13AT2 | – | +++ | ++ | +++ | +++ | ++ | +++ | +++ | +++ | ++ |
| Bif. bifidum | – | – | – | ± | – | – | – | + | ± | – |
| Bif. vulgatus | – | – | – | ± | – | ± | – | ± | + | – |
| Lact. fermentum KLD | – | – | – | – | – | – | – | ± | – | – |
| Lact. casei | – | – | – | – | – | – | – | ± | – | – |
| Lact. bulgaricus | – | – | – | – | – | – | – | – | – | – |

Bacterial identification:
X8AT2: Identified as Bifidobacterium, isolated from human faeces
Starch Identification:
1: A. 939 (D19) Hydroxypropylated; 2: A. 938 (C79) Acetylated; 3: A.961 (D8) Octenyl succinated; 4: A.955 (D2) Carboxymethylated; 5: A.960 (D7) Succinated; 6: HA 008 (D2118) Unmodified; 7: A993 D42 Succinated; 8: A956 (D1) Carboxymethylated; 9: A995 (D57) Acetylated; 10: A965 (D9) Hydroxypropylated;

TABLE 6

Adhesion of human bifidobacteria isolates and Lact. Fermentum KLD on the modified starch grantiles at pH 2.15

| Starches | 1 | 2 | 3 | 4 | 5 | 6 | 7 | 8 | 9 | 10 |
|---|---|---|---|---|---|---|---|---|---|---|
| X8AT1 | – | = | ± | ± | – | ± | = | = | – | ± |
| X8AT2 | = | + | ++ | ++ | ++ | +++ | ++ | ++ | + | ± |
| X13AT2 | ± | ++ | +++ | ++ | ++ | + | +++ | +++ | ++ | ++ |
| Lact. KLD | = | – | ± | – | ± | – | ± | + | – | – |

TABLE 7

The effects of growth media (glucose and Hi-maize ™ based) on the survival of Bifidobacterium X8AT1 in PBS buffer with various pH

| | Viable bacterial counts (log/10 ml) | | | | | |
|---|---|---|---|---|---|---|
| | pH 6.5 | | pH 3.5 | | pH 2.3 | |
| Times (h) | Glu | HM | Glu | HM | Glu | HM |
| 0 | 6.85 | 8.11 | 6.63 | 7.89 | ND | 6.68 |
| 3 | 6.45 | 7.73 | 0.00 | 5.64 | 0.00 | 0.00 |
| 6 | 6.54 | 7.47 | 0.00 | 5.37 | 0.00 | 0.00 |

TABLE 8

The effects of growth media (glucose and Hi-maize ™ based) on the survival of Bifidobacterium X8AT2 in PBS buffer with various pH

| | Viable bacterial counts (log/10 ml) | | | | | |
|---|---|---|---|---|---|---|
| | pH 6.5 | | pH 3.5 | | pH 2.3 | |
| Times (h) | Glu | HM | Glu | HM | Glu | HM |
| 0 | 6.14 | 7.80 | 6.38 | 7.75 | 6.07 | 6.88 |
| 3 | 5.98 | 5.99 | 3.48 | 6.67 | 0.00 | 0.00 |
| 6 | 5.54 | 7.92 | 0.00 | 5.24 | 0.00 | 0.00 |

TABLE 9

The effects of growth media (glucose and Hi-maize ™ based) on the survival of Bifidobacterium X13AT2 in PBS buffer with various pH

| | Viable bacterial counts (log/10 ml) | | | | | |
|---|---|---|---|---|---|---|
| | pH 6.5 | | pH 3.5 | | pH 2.3 | |
| Times (h) | Glu | HM | Glu | HM | Glu | HM |
| 0 | 6.94 | 8.16 | 6.75 | 6.80 | 7.04 | 6.88 |
| 3 | 6.92 | 7.97 | 6.50 | 5.44 | 0.00 | 0.00 |
| 6 | 7.05 | 8.05 | 0.00 | 4.50 | 0.00 | 0.00 |

The effects of bile acids on the survival of Bifidobacterium were previously grown in the medium containing glucose or Hi-maize™ starch. The three human bifidobacteria isolates showed better survival in the bile acids solution (Tables 10, 11 and 12). The cells which were previously collected from the medium contained Hi-maize™ starch which were more resistant in the high concentration of bile acids in comparison with the one obtained from the medium not containing Hi-maize™ starch.

TABLE 10

The effects of growth media (glucose and Hi-maize ™ based) on the survival of Bifidobacterium X8AT1 in PBS buffer with varied concentration of bile acids

| | Viable bacterial counts (log/10 ml) | | | | | |
|---|---|---|---|---|---|---|
| | 0.00% | | 0.03% | | 0.05% | |
| Times (h) | Glu | HM | Glu | HM | Glu | HM |
| 0 | 6.70 | 7.46 | 6.60 | 6.99 | 6.90 | 6.99 |
| 3 | 6.19 | 6.75 | 6.47 | 6.90 | 5.84 | 6.88 |
| 6 | 5.04 | 5.73 | 4.41 | 6.65 | 2.98 | 6.18 |

TABLE 11

The effects of growth media (glucose and Hi-maize ™ based) on the survival of Bifidobacterium X8AT2 in PBS buffer with varied concentration of bile acids

| | Viable bacterial counts (log/10 ml) | | | | | |
|---|---|---|---|---|---|---|
| | 0.00% | | 0.03% | | 0.05% | |
| Times (h) | Glu | HM | Glu | HM | Glu | HM |
| 0 | 6.78 | 7.04 | 6.80 | 7.05 | 6.95 | 6.92 |
| 3 | 6.90 | 6.94 | 6.84 | 6.03 | 6.70 | 7.08 |
| 6 | 6.74 | 6.60 | 6.88 | 7.16 | 5.21 | 7.13 |

TABLE 12

The effects of growth media (glucose and Hi-maize ™ based) on the survival of Bifidobacterium X13AT2 in PBS buffer with varied concentration of bile acids

| | Viable bacterial counts (log/10 ml) | | | | | |
|---|---|---|---|---|---|---|
| | 0.00% | | 0.03% | | 0.05% | |
| Times (h) | Glu | HM | Glu | HM | Glu | HM |
| 0 | 5.70 | 6.28 | 6.32 | 6.67 | 6.14 | 6.78 |
| 3 | 4.60 | 6.52 | 4.63 | 6.84 | 4.48 | 6.85 |
| 6 | 3.27 | 6.40 | 2.60 | 6.74 | 2.78 | 6.84 |

Comparative Survival Rates of Bifidobacterium X8AT2 Previosly Grown in Glucose and Hi-maize™ Starch in Mice Colon The comparative daily output of Bifidobacterium X8AT2 in the mice faeces was shown in Table 13. High recovery rates of Bif. X8AT2 were found in the group of mice fed with normal diet and dosed with bacteria grown in the Hi-maize™ starch medium, in comparison with the normal diet group of mice fed with glucose grown cells. The Hi-maize™ starch diet further enhanced the excreted numbers of Bif. X8AT2. Faecal daily wet weights would also be influenced by the diets. Hi-maize™ starch diet yielded the highest faecal output (Table 13), due to the high intake of feed.

Figure 11:
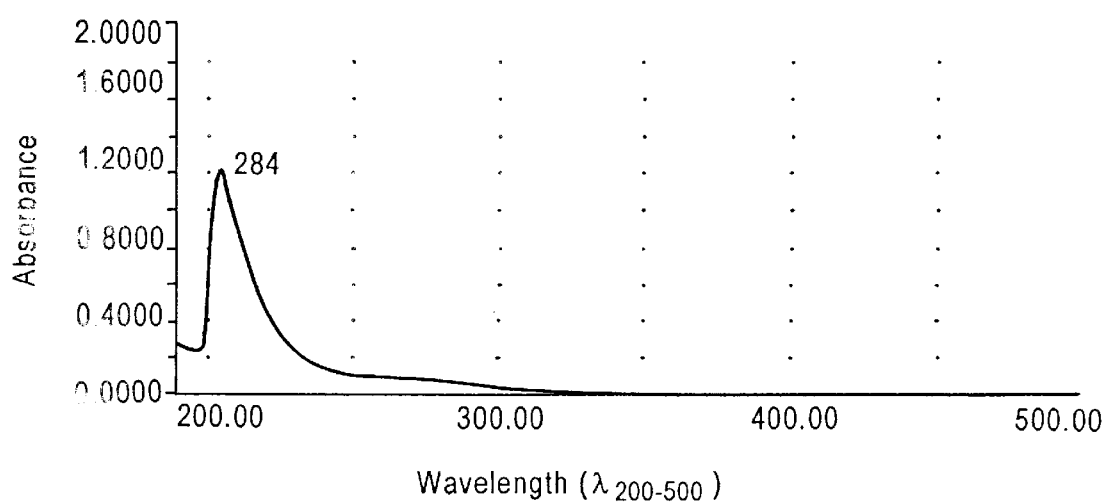
FIG. 11 shows verification of protein to which starch adhered.

The adhesion of bacterial surface proteins to starch granules was detected using a dot blot where fractions of spent culture supernatant and lithium chloride extracts were assayed for adhesion to Amylose starch granules (Sigma). Residual starch granules were detected by iodine. The spent culture supernatant $LiCl_2$ extracts of Bifidobacteria X13AT2 was extracted by gel filtration chromatography using Sephacryl S-300 (Pharmacia), and the Biologic chromatography system (Biorad). The relative molecular weight of the protein (FIG. 11) which showed affinity for the starch granules was estimated using molecular weight standards. The molecular weight of this component was between 50,000 and 60,000.

It can be seen from the above results that modifications influence the degree of attachment and that different species and different strains of the same genus attach to some modifications to different degrees. It is therefore be possible to make predictions as to which structures will favour attachment of selected probiotic microorganism. Furthermore it can be determined which structures are involved in the adhesion (allowing irreversible attachment if desired).

TABLE 13

The effect of Hi-maize ™ on in vivo survival of Bifidobacterium X8AT2

| | Groups | | |
|---|---|---|---|
| | 1 | 2 | 3 |
| | Diets | | |
| | Normal diet | Normal diet | Hi-maize ™ starch diet |
| Growth substrates for X8AT2 | Glucose | Hi-maize ™ starch | Hi-maize ™ starch |
| number dosed (Log 10) | 9.48[a] | 8.56[a] | 8.56[a] |
| number recovered (Log 10/10 h) | 7.14[b] | 7.43[b] | 7.51[b] |
| Recovery rates (per 1000) | 4.65 | 37.50 | 44.92 |
| Faecal weight (g) | 2.51 | 2.67 | 4.01 |

[a]log 10 CFU per day
[b]log 10 CFU per ml

Attached bacteria are known to be more resistant to antibiotics and it is therefore envisaged that since modifications of resistant starch allow attachment, that bacteria attached to the various modifications of the starches will be:
a. more resistant to conditions in the digestive tract namely low pH, bile acids and digestive enzymes. This will be a clear advantage for a delivery system designed to deliver viable probiotic bacteria to the stomach, small intestine or large intestine.
b. survive better in a preparation since they will be more resistant to environmental conditions in the formulated product.

c. identification of adhesions on the microbial surface and structures on the starch granules which are involved in irreversible attachment will have a range of applications not only for improving delivery of probiotic microbes but also in a further range of applications for attaching components to starches and derivatives thereof.

The present inventors have shown that particular modifications of resistant starch will favour attachment of particular microbes to the starch particles. This demonstrates that particular bacterial adhesions are involved and that these adhesions attach to structures on the starch. The various modifications tested allow one to predict the structures which are involved in specific and non-specific binding and which afford most resistance. In addition, some modifications or treatments will erode the granules to cause pitting and the resultant pits offer physical protection for the probiotics from the harsh environment.

Attachment to starch granules offers an advantage in stability and delivery of probiotic preparations since attachment to the granules will result in microbial preparations which are more stable. This would therefore apply during passage through the digestive tract and allow a more efficient delivery system as the attached microbes would be more resistant to the harsh conditions of the tract e.g. low pH, bile acids and digestive enzymes. This can be demonstrated in vitro by studying the survival of attached probiotic strains in buffer or growth media at various pH levels or containing digestive enzymes. In vivo confirmation can be obtained by studying survival after oral administration to humans, pigs or rodents.

EXAMPLE 6

Figure 12:
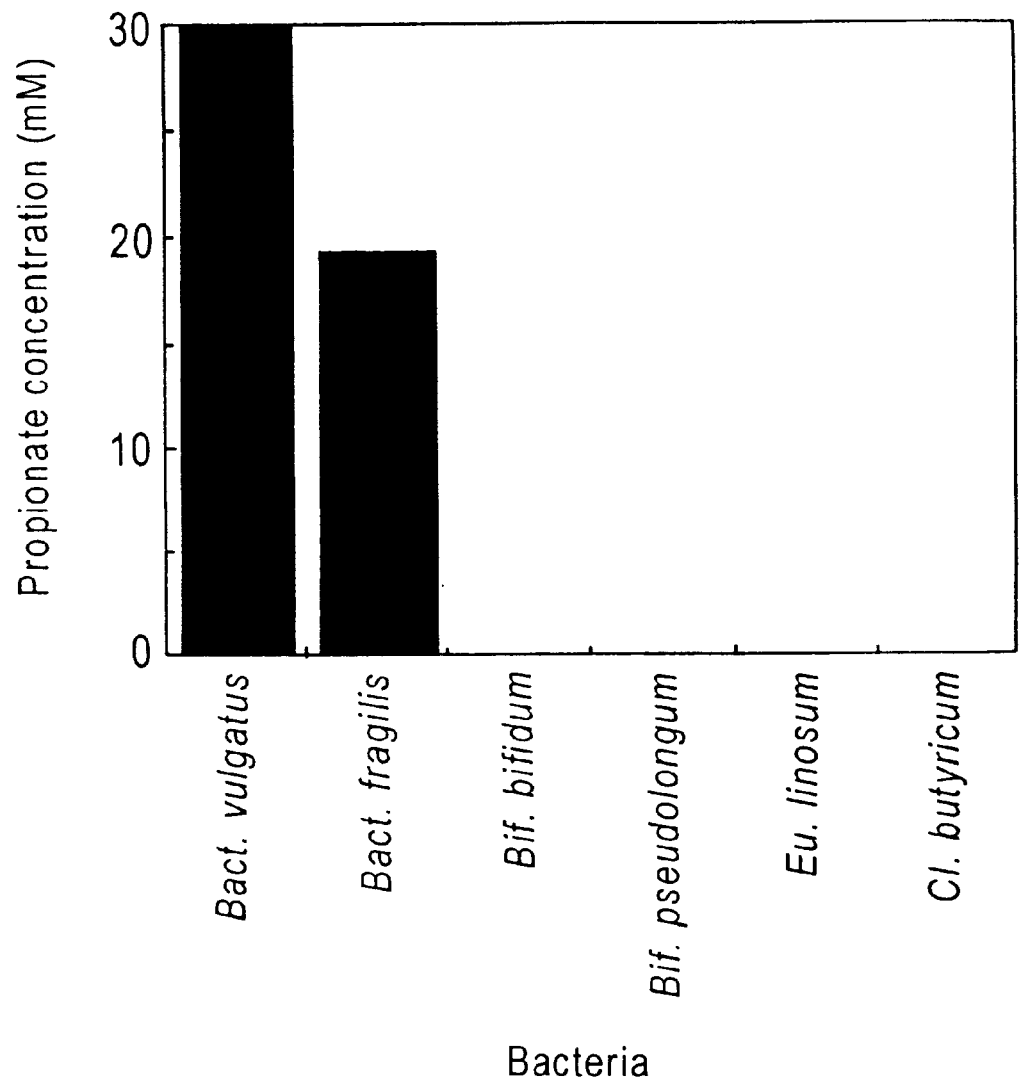
FIG. 12 shows levels of propionate production by a variety of bacteria.
Figure 13:
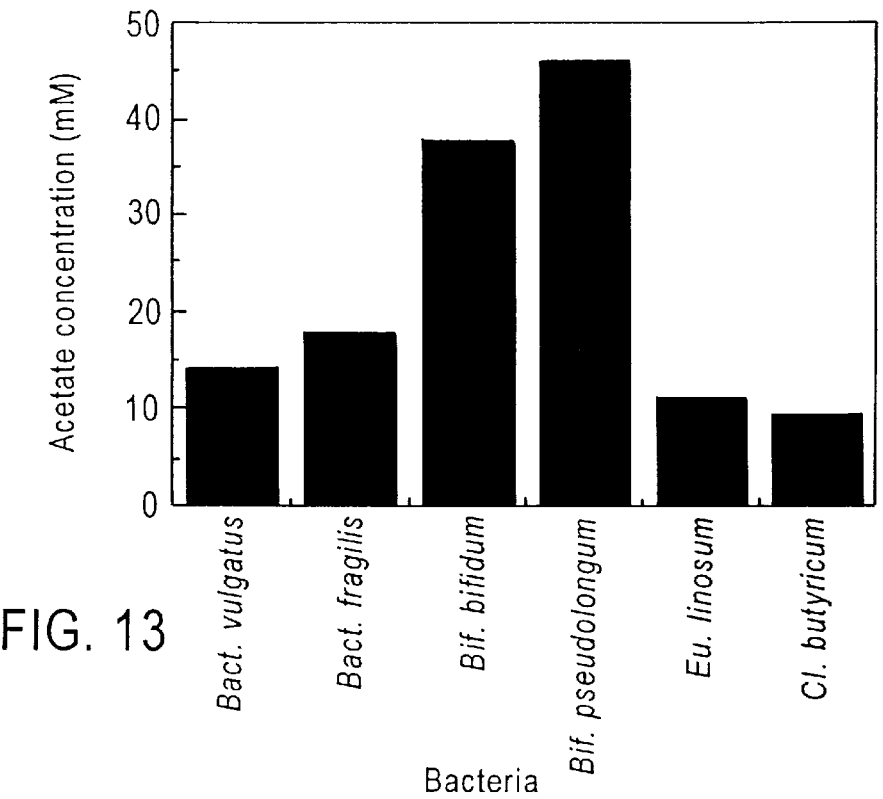
FIG. 13 shows levels of acetate production by a variety of bacteria.
Figure 14:
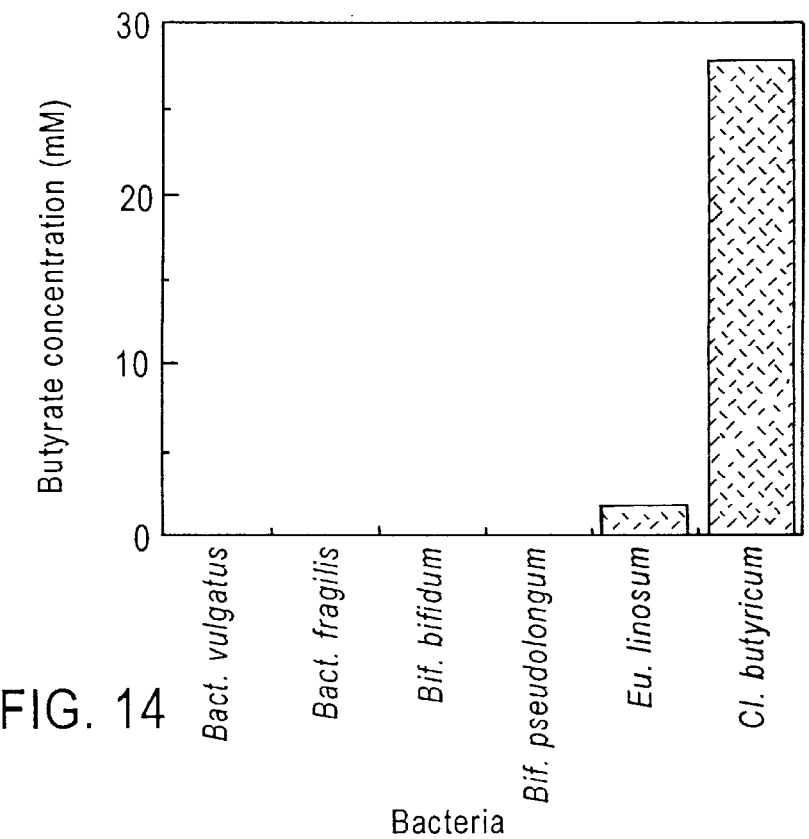
FIG. 14 shows levels of butyrate production by a variety of bacteria after 48 h incubation.

The medium included in Table 1 was used for studying growth of, and short chain fatty acid (SCFA) production by a range of intestinal isolates. Cultures were incubated anaerobically for 48 hours and the SCFA levels in the cultures were determined. The concentrations of propionate, acetate and butyrate for the various isolates are presented in FIGS. 12, 13 and 14, respectively.

It was shown that when resistant starch was the sole source of carbohydrate, high levels of acetate were produced by Bifidobacterium spp, high levels of propionate by *Bacteroides vulgatus* and *Bact. fragilis* while butyrate was produced to a limited extent by *Eubacterium linosum* and in large quantities by *Clostridium butyricum*.

EXAMPLE 7

Figure 15:
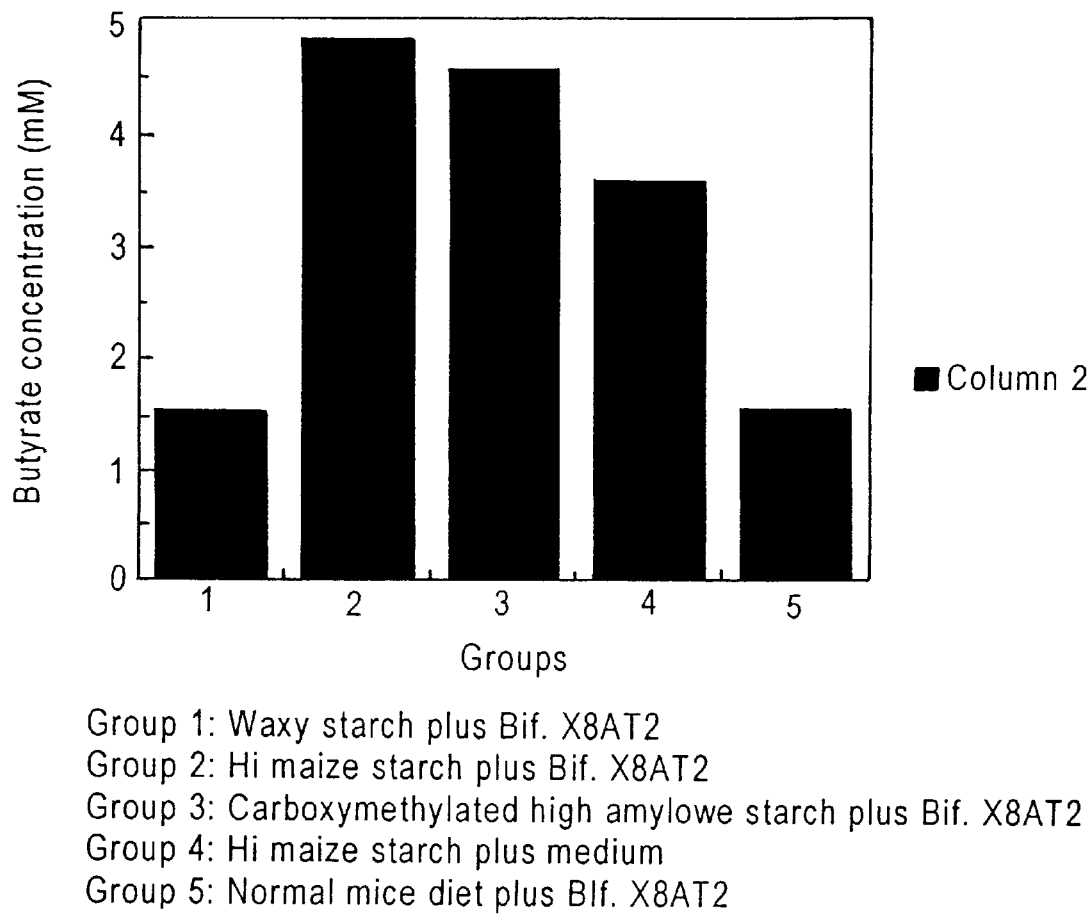
FIG. 15 shows butyrate concentrations in mice faeces after continuous feeding.

Mice were fed either normal mouse diet or a prepared diet containing either waxy starch, Hi-maize™ or modified Hi-maize™ and were orally dosed with 200 microliters of Bifidobacterium sp strain X8AT2 or *Bif. bifidum* cultures. The composition of the mouse prepared diet is included in Table 14. Faecal samples were collected at day zero and at day 8 after continuous feeding from day 3 to day 8 of the diet plus the bifidobacteria. Samples were stored frozen prior to analysis of SCFA. The results of the faecal butyrate levels are presented in FIG. 15. Elevated levels of butyrate were noted in mice fed resistant starch, or carboxymethylated resistant starch, together with Bifidobacterium sp strain X8AT2. Since these butyrate levels were higher than those noted in mice dosed with the resistant starch and *Bifidobacterium bifidum*, it was concluded that the elevation was not solely attributable to the resistant starch but rather the combination with the Bifidobacterium sp strain used.

TABLE 14

Diets for mice probiotic feeding experiments.

| Test Groups | A | B | C | D | E |
|---|---|---|---|---|---|
| Starch | Waxy | HA | Carboxy-methyl | HA | None |
|  | 400 | 400 | 400 | 400 |  |
| Casein | 200 | 200 | 200 | 200 |  |
| Canola oil | 25 | 25 | 25 | 25 |  |
| Sunflower oil | 25 | 25 | 25 | 25 |  |
| Sucrose | 150 | 150 | 150 | 150 |  |
| Wheat bran | 100 | 100 | 100 | 100 |  |
| Gelatin | 20 | 20 | 20 | 20 |  |
| Mineral mix | 67 | 67 | 67 | 67 |  |
| Vitamin mix | 13 | 13 | 13 | 13 |  |
| Methionine | 2 | 2 | 2 | 2 |  |
| Bacterial strain | X8AT2 | X8AT2 | X8AT2 | None | X8AT2 |

Waxy = waxy maize; HA = High amylose starch; Carboxy-methyl = Carboxymethylated high amylose starch. All weights are in grams. Bacterial cultures (200 microliters per day) were orally ingested by the mice with starch containing meals.

The fermentation end products of some dominant human intestinal bacteria after growth in a defined laboratory medium containing resistant starch were studied. It was shown that when resistant starch was the sole source of carbohydrate, high levels of acetate were produced by Bifidobacterium spp. high levels of propionate by *Bacteroides vulgatus* and *Bacteroides fragilis* while butyrate was produced to a limited extent by *Eubacterium linosum* and in large quantities by *Clostridium butyricum*. Consequently, dietary components including resistant starch and modifications thereof which allow selective enhancement of *Cl. butyricum* could be used to prevent colorectal cancer. This effect could be enhanced by oral administration of *Cl. butyricum* and Eubacterium, microbes of intestinal origin known to produce high levels of butyrate.

Furthermore, when resistant starch was orally dosed to mice in combination with Bifidobacterium spp, elevated levels of faecal butyrate were noted. The increased levels were also noted when a modified resistant starch was orally administered together with a Bifidobacterium sp. The elevated butyrate levels, however, are less marked for one strain of Bifidobacterium than another, indicative that it is the combination of the resistant starch and the Bifidobacterium rather than the starch alone which is the contributing factor to the elevated levels of butyrate.

Consequently, the invention covers the combination of resistant starch or modifications thereof with microorganisms such as Bifidobacterium spp, *Cl. butyricum,* Eubacterium as well as other SCFA including, butyrate, producing intestinal bacteria. Furthermore, since propionate can be absorbed and reach the liver where it can reduce de novo synthesis of cholesterol, one can postulate that oral administration of resistant starch and/or Bacteroides spp could yield a reduction of cholesterol levels.

Uses

The invention can be used in reducing the incidence of colorectal cancer and reducing colonic atrophy.

It will be appreciated by persons skilled in the art that numerous variations and/or modifications may be made to the invention as shown in the specific embodiments without departing from the spirit or scope of the invention as broadly described. The present embodiments are, therefore, to be considered in all respects as illustrative and not restrictive.

What is claimed is:

1. A method of altering the number, activity, or number and activity of a resident population of microorganism in a selected site of the gastrointestinal tract of an animal, the method comprising providing to the animal a selected modified or unmodified resistant starch or mixtures thereof in the form of high amylose starch selected from the group consisting of maize starch having an amylose content of 50% w/w or more, rice starch having an amylose content of 27% w/w or more, and wheat starch having an amylose content of 27% w/w or more, in combination with one or more probiotic microorganism such that upon ingestion the resistant starch passes through the gastrointestinal tract substantially unutilized until reaching the selected site of the gastrointestinal site where the resistant starch is utilized by the resident population of microorganism, the probiotic microorganisms or both the resident population and probiotic microorganisms thereby causing an alteration in number, activity, or number and activity of the resident population of microorganism.

2. The method according to claim 1 wherein the maize starch has an amylose content of 80% w/w or more.

3. The method according to claim 1 wherein the maize starch comprises particular granular size ranges of starches having enhanced resistant starch content.

4. The method according to claim 1 wherein the high amylose starch is modified chemically, enzymatically, physically, or mixture thereof.

5. The method according to claim 4 wherein the chemical modification is by cross-bonding, etherification, esterification, or acidification.

6. The method according to claim 4 wherein the physical modification is by crystallization.

7. The method according to claim 1 wherein the modified resistant starch is selected from the group consisting of hydroxypropylated starch, acetylated starch, octenyl succinated starch, carboxymethylated starch, and succinated starch.

8. The method according to claim 1 wherein the number, activity, or number and activity of the resistant population of microorganism is increased.

9. The method according to claim 1 wherein the number, activity, or number and activity of the resident population of microorganism is decreased.

10. The method according to claim 9 wherein the resident population of microorganism is a microbial pathogen.

11. The method according to claim 10 wherein the resistant starch acts as a carrier which functions to transport the one or more probiotic microorganisms to the selected site of the gastrointestinal tract, and which carrier acts as a growth or maintenance medium for non-pathogenic microorganism in the selected site of the gastrointestinal tract to an extent sufficient to suppress growth, activity, or growth and activity of the microbial pathogen.

12. The method according to claim 1 wherein the number of the probiotic microorganisms is increased.

13. The method according to claim 1 wherein the activity of the probiotic microorganism is increased.

14. The method according to claim 1 wherein the selected site in the gastrointestinal tract is the small intestine, stomach or large bowel.

15. The method according to claim 1 wherein the one or more probiotic microorganism, the resident population of microorganism, or the probiotic and resident population of microorganisms are bacteria which produce short chain fatty acids (SCFA).

16. The method according to claim 15 wherein SCFA is butyrate and the probiotic bacteria are *Clostridium butyricum,* Eubacterium, or mixture thereof.

17. The method according to claim 15 wherein the alteration in number, activity, or number and activity of the resident population of microorganism results in reducing the incidence of colorectal cancer or colonic atrophy in the animal.

* * * * *